United States Patent [19]

Poulsen et al.

[11] 4,206,284
[45] Jun. 3, 1980

[54] SACCHARIFICATION OF GLUCOSE RAFFINATE OR MOTHER LIQUORS

[75] Inventors: Poul Børge R. Poulsen; Susanne Rugh, both of Vaerløse; Barrie E. Norman, Farum, all of Denmark

[73] Assignee: Novo Industri A/S, Denmark

[21] Appl. No.: 851,709

[22] Filed: Nov. 15, 1977

[51] Int. Cl.$^2$ ............................................. C12D 13/02
[52] U.S. Cl. ........................................ 435/96; 435/94; 435/813
[58] Field of Search ..................... 195/31 R, 31 F, 13, 195/111; 127/46 A, 46 R, 46 B

[56] References Cited

U.S. PATENT DOCUMENTS

| 3,305,395 | 2/1967 | Scallet et al. | 195/31 F |
|---|---|---|---|
| 3,677,896 | 7/1972 | Kurimoto et al. | 195/31 R |
| 3,864,166 | 2/1975 | Barker et al. | 127/46 R |
| 4,011,137 | 3/1977 | Thompson et al. | 195/31 R |
| 4,017,363 | 4/1977 | McMullen et al. | 195/31 R |
| 4,025,357 | 5/1977 | Leiser et al. | 127/46 R |
| 4,069,104 | 1/1978 | Barker et al. | 195/31 R |

OTHER PUBLICATIONS

Nakamura et al., "Back Polymerization by Saccharifying Amylase", *Int. Chem. Eng.*, vol. 4, No. 3, (1964), pp. 530–534.

*Primary Examiner*—Thomas G. Wiseman
*Attorney, Agent, or Firm*—Fidelman, Wolffe & Waldron

[57] ABSTRACT

Saccharification of low DP polysaccharides of high glucose content syrups by short term contact with amyloglucosidase e.g. 1–10 hours, 1–10 AG units/gm of syrup solids, and syrup concentrations of 5–25 w/o solids in a batch saccharification, less than 30 minutes in a continuous process employing immobilized AMG.

Suitable high glucose content syrups are co-products that result from fractionation of isosyrup into 50+% d.s.b. fructose syrups and from production of crystalline dextrose.

4 Claims, 1 Drawing Figure

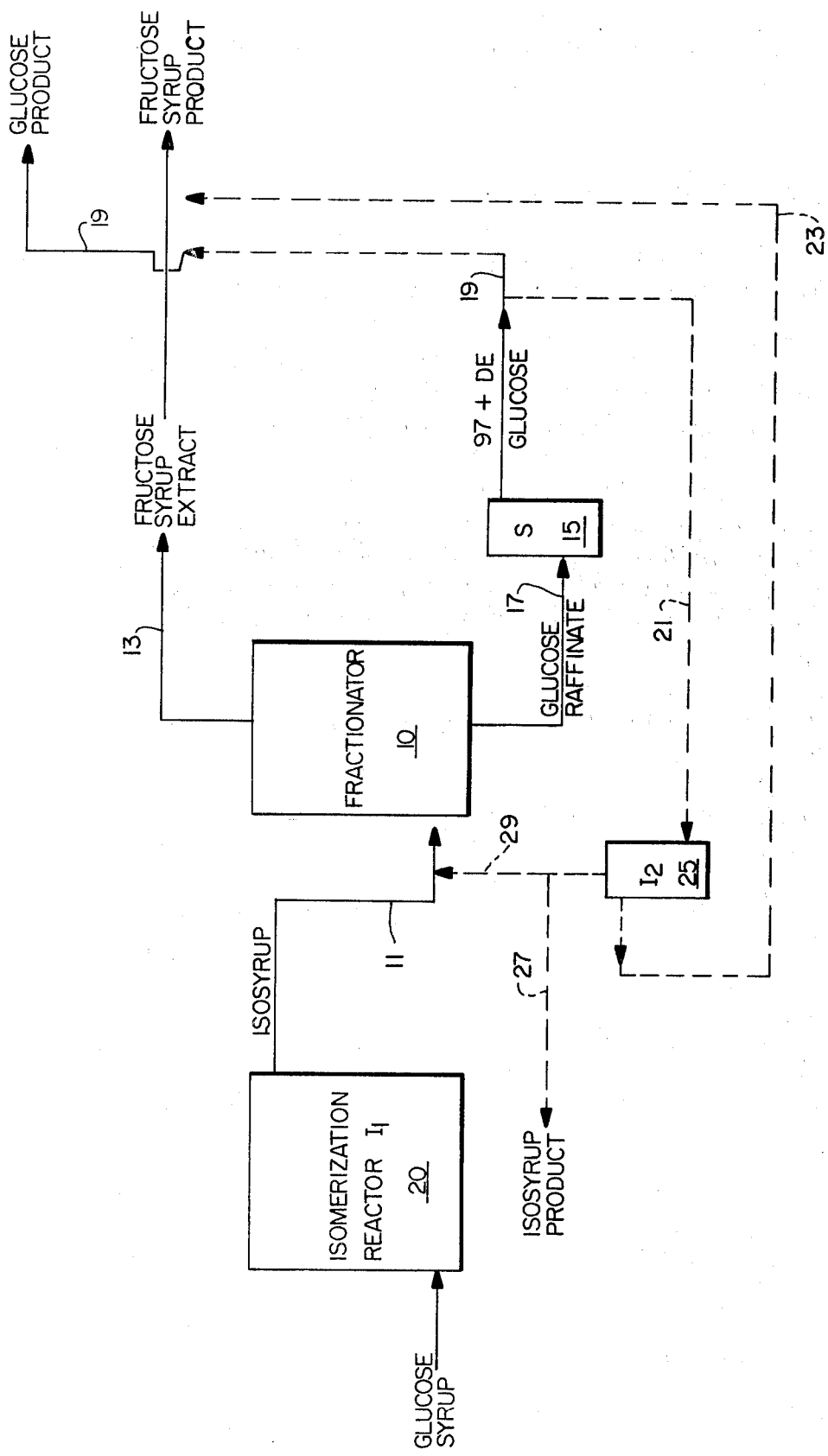

SACCHARIFICATION OF GLUCOSE RAFFINATE OR MOTHER LIQUORS

The carbohydrates available for large scale (food) use as sweetener materials are sucrose, glucose (or dextrose) and a glucose/fructose mixture known in the art as isosyrup. Sucrose, i.e. cane and beet sugar is the standard sweetener of commerce and to a very large extent its price level determines the market penetration of glucose and isosyrup into the sweetener market. However, price considerations may not be the controlling factor, as witness the usual situation wherein glucose is cheaper than isosyrup, and isosyrup is cheaper than sucrose yet the sweetener market employs more sucrose than isosyrup, and more isosyrup than glucose.

The sweetness factor must be taken into account. Glucose is less sweet than sucrose. Fructose, however, is sweeter than sucrose. Unfortunately, the enzymatic isomerization procedures employed to convert glucose into isosyrup can not exceed about 45% fructose d.s.b. (dry solids basis). A syrup having in excess of about 50% fructose d.s.b. is required to overcome the sweetness factor consideration.

An inexpensive fructose/glucose syrup with 55% fructose d.s.b., purportedly would have wide acceptance, in substitution for sucrose (for uses that do not accept the 42% fructose content isosyrup of commerce).

Fructose contents in excess of 50% d.s.b. can be achieved by application of adsorptive separation techniques to isosyrup for separating the isosyrup into a fructose extract and a glucose raffinate. Unfortunately, the isosyrup of commerce contains a significant polysaccharide content, e.g. 7%, and the bulk of the polysaccharides pass into the glucose raffinate. In consequence the fructose extract is quite pure, but the glucose raffinate contains, perforce, more polysaccharides than is usual in glucose syrups, and therefore is marketable only at some sort of discount from higher DE glucose syrups. Since economics (i.e. price of the sweetener) is such an important consideration to the market penetration of each sweetener substance, fractionation of isosyrup into a high fructose syrup extract must avoid any diminution in the sales value of the glucose raffinate co-product.

THE INVENTION

Briefly stated the present invention involves a multi-step process wherein a fructose-glucose syrup is fractionated into a fructose extract and a glucose/polysaccharide raffinate, and then the raffinate is saccharified. Optionally thereafter the raffinate is isomerized into a fructose-glucose syrup (i.e. isosyrup). Desirably the isomerized raffinate is added to the fructose extract, whereby only one product results, namely a 50+% fructose product which is higher in DE than the isosyrup starting material.

An important aspect of this invention is saccharification of a glucose syrup containing in excess of about 50% glucose d.s.b. and about 5;1 % di-, tri-and polysaccharides with an immobilized amyloglucosidase. One such a syrup is the glucose raffinate already described. Another such syrup arises (as a mother liquor) in the production of crystalline dextrose.

RATIONALE OF THE INVENTION

The isosyrup of commerce normally is described to the trade in terms of its fructose/glucose content (42% fructose) with presence of polysaccharides therein alluded to only incidentally in terms of its dextrose equivalent, e.g. DE 96. The polysaccharide content of DE 96 is about 7w/o d.s.b.

Thus fractionation of isosyrup so as to remove fructose will raise the polysaccharide content of what remains behind i.e. the glucose raffinate in some proportion to the extract/raffinate split. Since polysaccharides constitute a sweetness reducing and taste impairing impurity, their increased concentration in the glucose raffinate constitutes a detriment therein.

On the other hand, if concentration of the polysaccharide content of an isosyrup in a particular fraction were somehow found to be desirable, then their (inherent) concentration in the glucose raffinate would be an asset to the fructose/glucose separation system.

In point of fact, concentration of the polysaccharides in the raffinate is advantageous, because an increased concentration makes the polysaccharides more available for saccharification to glucose. The glucose raffinate fraction from an isosyrup fractionation system can be saccharified into a glucose product of higher purity than the DE-96 glucose initially employed to form the isosyrup.

According to practice of this invention an isosyrup is (adsorptively) fractionated into a 50+% fructose extract fraction and a glucose/polysaccharide raffinate fraction, and thereafter the raffinate is saccharified to a dextrose equivalent (DE) at least as high as the DE of the isosyrup starting material.

DISCUSSION OF THE INVENTION

In the least complex system contemplated for practice of this invention, namely fractionation of an isosyrup followed by saccharification of the glucose raffinate two high quality products result, i.e. 50+w/o fructose d.s.b., and a 96+DE glucose syrup.

If only a poor market for glucose exists (even for high quality glucose), then the glucose syrup, can be isomerized into an isosyrup of high quality i.e. 96+DE for marketing purposes.

In total practice of the present invention offers the art virtually complete design flexibility ranging from a two product system of good quality glucose or isosyrup and 50+w/o d.s.b. fructose clear through to a single product system for making 50+w/o d.s.b. fructose.

A one product of 50+w/o fructose can be produced by isomerizing the saccharified glucose raffinate and adding this isomerizate directly to the fructose extract. In theory, at least, a 65% fructose d.s.b. syrup will result from a single pass of isosyrup through a system including:

(1) fractionation
(2) raffinate saccharifier
(3) isomerizer

If the raffinate saccharifier were eliminated, then the fructose syrup would be much higher in polysaccharides, e.g. 7%, and slightly lower in fructose, and consequently the sweetness factor would be reduced and the taste would remain less agreeable.

The 55% fructose syrup alluded to above as readily marketable, can be obtained directly with a single pass of syrup through the system. However, recycling or multiple passes of raffinate through isomerization and fractionation can be made, and are contemplates for a one product system that produces a fructose syrup exceeding about 65 w/o d.s.b.

Basically the limiting criteria imposed upon practice of this invention are the criteria set by the fractionation per se, yet per se the fractionation separation of an isosyrup into a 50+% fructose extract and a glucose raffinate form no part of this invention. Several modes of fractionation have been proposed to the art, e.g. one is the "Sorbex" system by U.O.P. Inc. and one is proposed by Boehringer Mannheim GmbH (see U.S. Pat. No. 3,864,166). Suffice it here to say that fractionation of an isosyrup into a high fructose extract and a glucose/polysaccharide raffinate can be carried out by known to the art techniques and that the details of such fractionation form no part of this invention.

Saccharification of dextrins into high DE syrups are well known to the art and enzymatic saccharification is contemplated herein using the enzymes, pH, and temperature long established for conversion of dextrins. However, a glucose/polysaccharide raffinate is not the same as a dextrin and saccharification procedures explicitly adapted for the glucose/polysaccharide raffinate is herein described. The details of the saccharification procedure forms part of this invention.

Specifically the raffinate polysaccharides are low molecular weight, being very largely di-and tri-saccharides. In addition more than 50% glucose d.s.b. is present. The saccharifying enzymes available to the art to catalyze hydrolysis of polysaccharides into glucose are known to catalyse glucose dimerization into maltose and iso-maltose. Fortunately, saccharification proceeds quicker than the formation of isomaltose. The usual saccharification of dextrin commences with a low DE syrup, e.g. DE 10–30 with little or no glucose therein, a factor which minimizes the glucose reversion reaction, and enhances the saccharification reaction. The saccharifying circumstances adapted to dextrin saccharification are not as well adapted for the instance of a glucose/polysaccharide raffinate with its high glucose concentration and DP-2,3,4 polysaccharides.

It has been found that saccharification of a glucose/polysaccharide raffinate is most effective when carried out with high enzyme concentration, and with less concentrated syrup (vis a vis the usual dextrin, c.f. U.S. Pat. No. 4,017,363). Batch saccharification of a glucose/polysaccharide raffinate should be carried out with from 1–10 AG units/gm of syrup solids, for 1–10 hours and the syrup should be less than about 25 w/o solids, 5–25% solids is the range. The reaction temperatures range and pH range are the same as for saccharifying dextrins, i.e. 55°–60° C., pH 4.0–5.0.

A particularly preferred saccharifying method employs an immobilized Amyloglucosidase (AMG), reference being made to copending application Ser. No. 810,788 for disclosure of an immobilized AMG suitable for practice of this invention. The high AMG concentrations and short time contact period best suited to saccharifying a glucose/polysaccharide raffinate and like glucose syrups e.g. the mother liquor from dextrose crystallization processes.

Continuous saccharification of a glucose-polysaccharide raffinate is preferably conducted at a flow rate corresponding to 1 gm of dry solids per 1–30 AG units per hour (i.e. a contact time of 1–30 minutes). The syrup concentration should be less than ca. 25 w/o (d.s.b.), 5–25 w/o (d.s.b.) being the preferred range. Typical temperature and pH conditions of the column reaction are in the range of 50°–60° C. and 3.5–7.0, respectively.

DETAILED PRACTICE OF THE INVENTION

For further understanding of this invention, reference is now made to the attached drawing wherein the single FIGURE illustrates the process of this invention in block form. The drawing also illustrates (in block form) how the process of this invention interfits with the conversion of glucose syrups into isosyrup.

Referring now to the drawing, it may be seen that fractionator 10 receives an iso-syrup feed from line 11 and discharges a fructose extract into line 13, and a glucose and polysaccharide raffinate into line 17. The fructose content of glucose enzymatically isomerized, e.g. in isomerizer 20 into the isosyrup feed will not exceed about 45%, and for exemplary purposes commercial quality isosyrup of 42% fructose, 51.3% glucose and 6% polysaccharides may be considered typical of the available fructose/glucose syrups.

The details of the fractionator are not illustrated. The fractionation per se forms no part of this invention. Several modes of fructose separation systems are known to the art, with at least one offered on a commercial basis (i.e. "Sorbex" by UOP). Suffice it then to say only that fractionator 10 operates on adsorption principles, and separates the feed stream iso-syrup into a fructose extract having more than 50% fructose d.s.b. The fructose content of the extract can be predetermined as desired (since such flexibility is one attribute of this invention), but for exemplary purposes will be illustrated at 55% and 80% fructose d.s.b. For illustrative purposes the ultimate fructose content of the syrup product of this invention will be 55% fructose d.s.b.

The saccharifier 15 into which the raffinate glucose/polysaccharide stream flows by way of line 17 is either a batch process or a continuous immobilized enzyme column as has been described above and exemplified hereafter. In either event the saccharifier 15 is adapted to convert the polysaccharide content of the raffinate into glucose as quickly as is reasonably possible, and to do so before the enzyme catalyzed reversion of glucose to maltose and isomaltose becomes material.

Flow of the saccharified raffinate from saccharifier 15 by way of line 19 out of the system is illustrated in the drawing to show that the glucose may be a product of the system. However, several of the uses to which the saccharified raffinate may be put according to practice of this invention, are illustrated also. Thus the saccharified raffinate leaving saccharifier 15 by way of line 19 may be passed to isomerizer 25 by way of line 21. Then after isomerization the raffinate isosyrup may be passed by way of line 23 for addition to the fructose extract. Since, the saccharified raffinate is isomerized into an iso-syrup of purity equal to or better than the iso-syrup heretofore offered to the trade, the syrup can be removed by line 27 as a product of the system. A third alternative illustrated in the drawing is to send to isomerizate through line 29 into fractionator 10.

For further understanding of this invention conversion of a typical iso-syrup into 55% fructose d.s.b. will be illustrated with fractionation conditions (Sorbex system) productive of 55% and 80% fructose d.s.b. (The iso-syrup feed contained 42% fructose, 53% glucose, 1.5% maltose/maltulose, 1.5% isomaltose and 2% DP3+ d.s.b.

1. 1000 pounds/hr d.s.b. of iso-syrup solids from isomerizer 20 is fractionated in fractionator 10 into 452 lbs/hr of an extract containing 90% fructose and 10% glucose and 548 lbs/hr of a raffinate containing 88.6% glucose, 2.3% fructose 2.7% maltose/maltulose, 2.7% isomaltose and 3.7% DP3+.

Saccharification of this raffinate in saccharifier 15 results in a glucose syrup containing 0.3% maltose/maltulose, 3.0% isomaltose, 0.4% DP3+, 2.3% fructose and 94.0% glucose, a subsequent isomerization in isomerizer 25 produces an iso-syrup of 26.1% fructose, 70.2% glucose and 3.7% polysaccharides. This stream is now mixed with the extract stream 13, resulting in a 98 DX product of the following composition: 55% fructose, 43% glucose and 2% polysaccharides. It is remarkable that this 55% fructose product is of greater purity than the isosyrup feed stream.

If a product with a fructose content of more than about 65% is desired the isosyrup from isomerizer 25 is recycled by way of line 29 back into the fractionation.

2. 1000 lbs/hour d.s.b. of isosyrup from isomerizer 20 is mixed with stream 29 (1010 lbs/hour) from the raffinate isomerizer 26 before being fractionated into 1000 lbs/hour of a fructose extract having 80% fructose, 17.4% glucose, 0.5% maltose/maltulose, 1.8% isomaltose and 0.3% DP3+ (corresponding to 98.6 DE) and 1010 lbs/hour of a glucose raffinate having 2.3% fructose, 90.2% glucose, 2.0% maltose/maltulose, 3.0% isomaltose and 2.5% DP3+. Saccharification of this raffinate in saccharifier 15 results in a glucose syrup containing 2.3% fructose, 92.7% glucose, 1.0% maltose/maltulose, 3.3% isomaltose and 0.7% DP3+. A subsequent isomerization of the raffinate to 40% fructose d.s.b. is made before this stream (29) is mixed with stream 11.

For further understanding of this invention reference is now made to the following specific examples.

EXAMPLE I

Comparison between Saccharification of Raffinate By Soluble AMG and By Immobilized AMG The saccharification of a raffinate consisting of 84.3% Glucose, 2.9% Fructose, 9.4% maltose, 0.5% isomaltose and 2.9% maltotriose and higher polymers was performed in a batch operation under the following conditions: 20.6% w/w dry solid, 60° C. and pH 4.5. The following experimental results were obtained.

Table IA

| | 5000 ml batch 20 ml AMG 150 | | | | 5000 ml batch 10 ml AMG 150 | | | |
|---|---|---|---|---|---|---|---|---|
| Hours | Monosacc | Maltose | Iso-malt | DP3+ | Monosacc | Maltose | Iso-malt | DP3+ |
| 0 | 87.2 | 9.4 | 0.5 | 2.9 | 87.2 | 9.4 | 0.5 | 2.9 |
| 0.17 | 91.8 | 4.9 | 0.5 | 2.8 | 91.0 | 6.1 | 0.5 | 2.4 |
| 0.50 | 95.6 | 1.2 | 0.6 | 2.6 | 95.9 | 2.3 | 0.5 | 1.3 |
| 1.00 | 97.1 | 0.6 | 0.6 | 1.7 | 96.6 | 1.2 | 0.6 | 1.6 |
| 2.00 | 98.3 | 0.6 | 0.7 | 0.3 | 97.5 | 0.8 | 0.7 | 0.9 |
| 5.00 | 98.5 | 0.1 | 0.9 | 0.4 | 97.7 | 1.1 | 0.9 | 0.3 |
| 23.17 | 93.0 | 0.0 | 4.7 | 2.4 | 95.9 | 0.0 | 3.5 | 0.7 |

A raffinate with the same composition was then saccharified in a fixed bed column operation.

The IAMG was produced according to example 2 in patent application Serial No. 810,788 filed June 28, 1977. The following conditions were applied: 20.6 w/w% dry solid, 55° C. and pH 4.5.

The following experimental results were obtained:

| Space Time | Flow ml/hr | Product Composition, % | | | |
|---|---|---|---|---|---|
| | | DX | Maltose | Iso-Maltose | DP3+ |
| 4.7 minutes | 181 | 96.4% | 1.2 | 0.6 | 1.8 |
| 7.5 minutes | 113 | 97.2% | 1.0 | 0.6 | 1.2 |
| 10.0 minutes | 85 | 97.8% | 0.8 | 0.8 | 0.6 |
| 20.0 minutes | 43 | 96.9% | 0.7 | 2.0 | 0.4 |
| 37.5 minutes | 23 | 93.6% | 1.3 | 4.0 | 1.2 |

Inlet raffinate composition: as above
column size: 2.5 cm(d) by 40 cm(h)
Amount of IAMG: 5g The product composition was determined by HPLC.

EXAMPLE II

Long Time Saccharification of Raffinate by IAMG

The saccharification of a raffinate consisting of 84.4% Glucose, 2.8% Fructose, 8.9% maltose, 1.0% iso-maltose and 2.9% maltotriose and higher polymers was carried out in a fixed fed column of IAMG under the following conditions:

5 g IAMG (as in example I)
Column 2.5 cm(d), 40 cm(h)
20.6 w/w% dry solid
55° C., pH 4.5
Constant flow rate 175 ml/hour, contact time 5 min.

| Time (days) | Product Composition | | | |
|---|---|---|---|---|
| | Monosacch. | Maltose | Isomaltose | DP3+ |
| 1 | 97.4% | 0.6% | 1.2% | 0.8% |
| 3 | 97.0% | 1.0% | 1.1% | 0.9% |
| 6 | 96.0% | 2.0% | 1.2% | 0.8% |
| 10 | 95.7% | 1.5% | 1.3% | 1.5% |
| 15 | 94.5% | 2.7% | 1.1% | 1.7% |
| 20 | 93.9% | 2.9% | 1.2% | 2.0% |
| 27 | 93.5% | 2.6% | 1.3% | 2.6% |
| 30 | 93..0% | 3.0% | 1.2% | 2.8% |

EXAMPLE III

Influence of Temperature on IAMG activity and Stability

Conditions as in Example II

| Temperature | Initial Product Composition | | | | Days to reach 93.3% Monosacch. |
|---|---|---|---|---|---|
| | Monosacch. | Maltose | Isomaltose | DP3+ | |
| 55° C. | 97.4% | 0.6% | 1.2% | 0.8% | 28 |
| 60° C. | 97.5% | 0.6% | 1.2% | 0.7% | 9 |

-continued

| | Initial Product Composition | | | | Days to reach 93.3% Mono- sacch. |
|---|---|---|---|---|---|
| Tem- perature | Mono- sacch. | Mal- tose | Iso- mal- tose | DP3+ | |
| 65° C. | 97.9% | 0.7% | 1.1% | 0.8% | 6 |

EXAMPLE IV

Comparison Between Saccharification of a Mother Liquor With a High Isomaltose Content By Soluble AMG and By Immobilized AMG Conditions as in Example I, but Mother Liquor composition: Fructose 1.1%, Glucose 65.3%, 13.4% Maltose, 10.0% Isomaltose, 2.5% DP3 and 7.7% DP4+.

Saccharification with Soluble AMG:

| | 5000 ml Batch 20 ml AMG 150 | | | |
|---|---|---|---|---|
| Hours | Monosacc | Maltose | Isomalt | DP3+ |
| 0 | 66.4% | 13.4% | 10.0% | 10.2% |
| 0.17 | 69.3% | 11.7% | 10.3% | 8.7% |
| 0.50 | 72.1% | 10.4% | 10.5% | 7.0% |
| 1.00 | 76.7% | 6.5% | 10.8% | 6.0% |
| 2.00 | 80.1% | 3.9% | 11.2% | 4.8% |
| 5.00 | 82.0% | 2.3% | 11.3% | 4.4% |
| 23.17 | 84.5% | 0.3% | 13.2% | 2.0% |

Saccharification with IAMG:

| | | Product Composition | | | |
|---|---|---|---|---|---|
| Space Time | Flow | Monosacc | Maltose | Isomalt | DP3+ |
| 4.7 min | 180 ml/h | 81.6% | 3.0% | 10.2% | 5.2% |
| 7.5 min | 112 ml/h | 82.8% | 2.3% | 10.4% | 4.5% |
| 10.0 min | 95 ml/h | 84.0% | 1.8% | 10.5% | 3.7% |
| 20.0 min | 45 ml/h | 82.0% | 1.1% | 11.0% | 4.6% |

EXAMPLE V

Comparison between saccharification of raffinate by soluble AMG and by immobilized AMG The saccharification of a raffinate consisting of 83.9% glucose, 3.3% fructose, 6.2% maltose, 3.1% isomaltose and 3.4% maltotriose and higher polymers was performed in a batch operation under the following conditions: 20.5% w/w dry solid, 60° C. and pH 4.5. The following experimental results were obtained.

| | 5000 ml batch, 20 ml AMG 150 | | | |
|---|---|---|---|---|
| Hours | Monosacch. | Maltose | Isomaltose | DP3+ |
| 0 | 87.3 | 6.2 | 3.1 | 3.4 |
| 0.17 | 92.0 | 2.5 | 3.1 | 2.4 |
| 0.33 | 92.8 | 2.0 | 3.2 | 2.0 |
| 0.50 | 93.9 | 1.4 | 3.2 | 1.5 |
| 1 | 94.9 | 1.1 | 3.4 | 0.6 |
| 2 | 94.8 | 0.9 | 3.5 | 0.8 |
| 22 | 91.8 | 0.1 | 6.0 | 2.1 |

A raffinate with the same composition was then saccharified in a fixed bed column operation.

The IAMG was produced according to example 2 in patent application Serial No. 810,788 filed June 28, 1977. The following conditions were applied: 20.5 w/w% dry solid, 55° C. and pH 4.5.

The following experimental results were obtained:

| Space time minutes | Flow ml/hour | Product composition, % | | | |
|---|---|---|---|---|---|
| | | DX | Maltose | Isomaltose | DP3+ |
| 5.6 | 170 | 94.2 | 1.3 | 3.2 | 1.3 |
| 8.2 | 117 | 94.7 | 1.1 | 3.2 | 1.0 |
| 13.5 | 71 | 95.1 | 0.9 | 3.4 | 0.6 |
| 18.6 | 52 | 95.3 | 0.7 | 3.5 | 0.5 |
| 25.6 | 37 | 95.1 | 0.6 | 3.6 | 0.7 |

Inlet raffinate composition: as above
Column size: 2.5 cm(d) by 40 cm(h)
Amount of IAMG: 5g The product composition was determined by HPLC.

EXAMPLE VI

Long Time Saccharification of Raffinate by IAMG

The saccharification of a raffinate consisting of 83.9% glucose, 3.3% fructose, 6.2% maltose, 3.1% isomaltose and 3.4% maltotriose and higher polymers was performed in a fixed bed column operation by use of IAMG under the following conditions:

5 g IAMG (as in example I)
Column 2.5 cm (d), 40 cm (h)
20.6 w/w% dry solid
55° C., pH 4.5
Constant flow rate 175 ml/hour, contact time 5 min.

| Time (days) | Product composition, % | | | |
|---|---|---|---|---|
| | Monosacch. | Maltose | Isomaltose | DP3+ |
| 1 | 94.5 | 1.0 | 3.3 | 1.2 |
| 3 | 94.0 | 1.3 | 3.4 | 1.3 |
| 6 | 93.8 | 1.5 | 3.2 | 1.5 |
| 9 | 93.3 | 1.7 | 3.3 | 1.7 |
| 11 | 92.9 | 2.0 | 3.3 | 1.8 |

What is claimed is:

1. A method for saccharifying a glucose syrup containing therein at least about 5% w/w d.s.b. of disaccharides and trisaccharides and at least about 50% glucose d.s.b. which comprises batch saccharifying the glucose syrup with amyloglucosidase at saccharifying temperature and pH conditions with 1–10 AG units/gm of syrup solids for 1–10 hours, the glucose syrup (concentration) being less than about 25% (w/w) by weight solids.

2. The method of claim 1 wherein the glucose syrups concentration is 5–25% by weight solids.

3. A continuous process for saccharifying a glucose syrup containing therein at least about 5% w/w d.s.b. of disaccharides and trisaccharides and 50% glucose d.s.b. which comprises passing the glucose syrup into contact with an immobilized amyloglucosidase under saccharifying temperature and pH conditions for a total contact time of less than 30 minutes, the glucose syrup concentration being less than about 25% by weight solids.

4. The process of claim 3 wherein the glucose syrup concentration is 5–25% by weight solids.

* * * * *